(12) United States Patent
Fortier et al.

(10) Patent No.: US 8,468,708 B2
(45) Date of Patent: Jun. 25, 2013

(54) HEMOSTATIC PATCH (71) Applicant: Confluent Surgical, Inc., Bedford, MA (US)

(72) Inventors: Jason Fortier, Concord, MA (US); Les Hull, Attleboro, MA (US)

(73) Assignee: Confluent Surgical, Inc., Bedford, MA (US)

( * ) Notice: Subject to any disclaimer, the term of this patent is extended or adjusted under 35 U.S.C. 154(b) by 0 days.

(21) Appl. No.: 13/645,158

(22) Filed: Oct. 4, 2012

(65) Prior Publication Data

US 2013/0025428 A1 Jan. 31, 2013

Related U.S. Application Data (63) Continuation of application No. 13/013,344, filed on Jan. 25, 2011, now Pat. No. 8,302,323, which is a continuation-in-part of application No. 12/819,323, filed on Jun. 21, 2010.

(51) Int. Cl.
*G01B 3/14* (2006.01)
(52) U.S. Cl.
USPC ............................................. 33/562
(58) Field of Classification Search
USPC .................................. 33/562, 563
See application file for complete search history.

(56) References Cited

U.S. PATENT DOCUMENTS

| 684,142 | A | * | 10/1901 | Ward ................................ 33/562 |
| 2,500,873 | A | * | 3/1950 | Sager ............................... 33/563 |
| 3,364,200 | A | | 1/1968 | Ashton et al. |
| 4,595,203 | A | * | 6/1986 | DeLano et al. ................. 33/562 |
| 4,626,253 | A | | 12/1986 | Broadnax, Jr. |
| 4,725,279 | A | | 2/1988 | Woodroof |
| 5,201,745 | A | | 4/1993 | Tayot et al. |
| 5,484,495 | A | * | 1/1996 | Moore ............................ 33/563 |
| 5,484,913 | A | | 1/1996 | Stilwell et al. |
| 5,511,316 | A | * | 4/1996 | Fischer et al. ................. 33/562 |
| 5,577,328 | A | * | 11/1996 | Kerry, Sr. ........................ 33/563 |
| 5,702,715 | A | | 12/1997 | Nikolaychik et al. |
| 6,152,943 | A | | 11/2000 | Sawhney |
| 6,165,201 | A | | 12/2000 | Sawhney et al. |
| 6,179,862 | B1 | | 1/2001 | Sawhney |

(Continued)

FOREIGN PATENT DOCUMENTS

| EP | 2 143 737 | 1/2010 |
| EP | 2143737 | 1/2010 |

(Continued)

OTHER PUBLICATIONS

European Search Report for EP 09252417.2-1219 mailed Dec. 10, 2010.

(Continued)

*Primary Examiner* — G. Bradley Bennett (57) ABSTRACT

The present disclosure relates to a surgical patch and methods of using the same. The surgical patch includes a body having a substrate, a longitudinal slit bisecting at least a portion of the body, and at least one additional slit extending from the longitudinal slit defining a retractable section. The surgical patch of the disclosure may be used, for example, to provide hemostasis at a site of anastomosis. The present disclosure also provides kits including such surgical patches, as well as templates that permit one to cut the patch to a desired size and/or shape.

13 Claims, 11 Drawing Sheets

U.S. PATENT DOCUMENTS

| | | |
|---|---|---|
| 6,443,964 B1 | 9/2002 | Ory et al. |
| 6,500,777 B1 | 12/2002 | Wiseman et al. |
| 6,514,534 B1 | 2/2003 | Sawhney |
| 6,566,406 B1 | 5/2003 | Pathak et al. |
| 6,603,054 B2 | 8/2003 | Chen et al. |
| 6,605,294 B2 | 8/2003 | Sawhney |
| 6,638,296 B2 | 10/2003 | Levinson |
| 6,673,093 B1 | 1/2004 | Sawhney |
| 6,703,047 B2 | 3/2004 | Sawhney et al. |
| 6,726,696 B1 | 4/2004 | Houser et al. |
| 6,818,018 B1 | 11/2004 | Sawhney |
| 6,890,344 B2 | 5/2005 | Levinson |
| 6,921,412 B1 | 7/2005 | Black et al. |
| 6,939,364 B1 | 9/2005 | Soltz et al. |
| 7,009,034 B2 | 3/2006 | Pathak et al. |
| 7,021,086 B2 | 4/2006 | Ory et al. |
| 7,329,792 B2 | 2/2008 | Buckman et al. |
| 7,347,850 B2 | 3/2008 | Sawhney |
| 7,792,764 B2 * | 9/2010 | Collings ............... 33/562 |
| 8,302,323 B2 * | 11/2012 | Fortier et al. ............ 33/562 |
| 2001/0045022 A1 * | 11/2001 | Lariviere, Jr. et al. ....... 33/562 |
| 2002/0106409 A1 | 8/2002 | Sawhney et al. |
| 2003/0031697 A1 | 2/2003 | Chudzik et al. |
| 2003/0093075 A1 | 5/2003 | Levinson |
| 2003/0093115 A1 | 5/2003 | Levinson |
| 2005/0165445 A1 | 7/2005 | Buckman et al. |
| 2005/0222615 A1 | 10/2005 | Levinson |
| 2006/0013863 A1 | 1/2006 | Shalaby et al. |
| 2007/0276308 A1 | 11/2007 | Huey et al. |
| 2008/0114092 A1 | 5/2008 | Sawhney |
| 2008/0114394 A1 | 5/2008 | Houser et al. |
| 2008/0132820 A1 | 6/2008 | Buckman et al. |
| 2009/0205216 A1 * | 8/2009 | Ai ...................... 33/563 |
| 2010/0100123 A1 | 4/2010 | Bennett |
| 2011/0070288 A1 | 3/2011 | Andjelic |

FOREIGN PATENT DOCUMENTS

| | | |
|---|---|---|
| EP | 2177239 | 4/2010 |
| EP | 2179753 | 4/2010 |
| EP | 2 196 193 | 6/2010 |
| EP | 2196193 | 6/2010 |
| EP | 2 233 160 | 9/2010 |
| EP | 2 233 161 | 9/2010 |
| EP | 2233160 | 9/2010 |
| EP | 2233161 | 9/2010 |
| WO | WO 2004/041313 | 5/2004 |
| WO | WO 2010/043980 | 4/2010 |

OTHER PUBLICATIONS

European Search Report for EP 09252421.4-1219 mailed Dec. 10, 2010.

International Search Report issued in Application EP 11250562.3 dated Nov. 28, 2011.

International Search Report issued in Application EP 11250564.9 dated Nov. 30, 2011.

International Search Report issued in Application EP 11250563.1 dated Dec. 20, 2011.

International Search Report issued in Application EP 11250566.4 dated Dec. 13, 2011.

International Search Report issued in Application EP 11250565.6 dated Dec. 13, 2011.

European Search Report for EP 09252417.2-1219 mailed Dec. 12, 2010.

European Search Report for EP 09252421.4-1219 mailed Dec. 12, 2010.

International Search Report issued in Application EP 11250562.3 mailed Dec. 8, 2011.

International Search Report issued in Application EP 11250564.9 mailed Dec. 8, 2011.

International Search Report issued in Application EP 11250563.1 mailed Dec. 27, 2011.

International Search Report issued in Application EP 11250566.4 mailed Dec. 22, 2011.

International Search Report issued in Application EP 11250565.6 mailed Dec. 23, 2011.

* cited by examiner

HEMOSTATIC PATCH

CROSS-REFERENCE TO RELATED APPLICATIONS

This application is a continuation of U.S. patent application Ser. No. 13/013,344, now U.S. Pat. No. 8,302,323 which, in turn, is a continuation-in-part application of co-pending U.S. patent application Ser. No. 12/819,323, filed on Jun. 21, 2010, the entire disclosures of each of which are hereby incorporated by reference in their entirety.

BACKGROUND

The present disclosure relates to implants and, more particularly, to patches suitable for achieving hemostasis.

In situ hemostatic therapy has primarily focused on the transformation of precursor solutions into solids within a patient's body. The transformation of these precursors may be achieved in a variety of ways, including precipitation, polymerization, crosslinking, and desolvation. However, limitations exist when using solutions for in situ hemostatic therapy. For example, solutions of low viscosity may flow away and be cleared from an application site before transformation and solidification occurs. Furthermore, formulation of the solutions may be complex, as their preparation may require reconstitution of precursors, or, when the solutions are stored frozen, thawing. Moreover, certain surgeries, including those dealing with the joining of tubular structures in the body, (e.g., anastomoses), do not lend themselves to the use of liquid hemostatic therapies.

It would thus be beneficial to provide an implantable device capable of adhering and providing hemostatic therapy to physiological structures to which a solid device may not easily adhere.

SUMMARY

The present disclosure relates to surgical patches, cutting templates suitable for customizing the shapes of the surgical patches, and methods of forming surgical patches with these templates.

In embodiments, a cutting template of the present disclosure may include a top portion possessing at least one slit forming a desired pattern; a bottom portion possessing openings corresponding to the pattern in the top portion, the bottom portion further including a recessed region capable of holding a surgical patch therein; and a means for connecting the top portion to the bottom portion.

In other embodiments, a cutting template of the present disclosure may include a top portion possessing slits forming a star pattern; a bottom portion possessing openings corresponding to the star pattern present in the top portion, the bottom portion further including a recessed region capable of holding a surgical patch therein; and a means for connecting the top portion to the bottom portion.

As noted above, methods for using cutting templates to form surgical patches are also provided. In embodiments, a method of the present disclosure includes providing a cutting template including a top portion possessing at least one slit forming a desired pattern, a bottom portion possessing openings corresponding to the at least one slit present in the top portion, and a means for connecting the top portion to the bottom portion, the bottom portion further including a recessed region capable of holding a surgical patch therein; introducing a surgical patch into the recessed region in the bottom portion; passing a cutting device through the at least one slit in the top portion, the surgical patch, and the openings in the bottom portion, thereby cutting the surgical patch in the pattern of the at least one slit and openings; removing the top portion of the template from the bottom portion of the template; and removing the surgical patch possessing the pattern from the cutting template.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION

The present disclosure provides surgical implants which, in embodiments, may be suitable to promote hemostasis. In embodiments, the present disclosure provides in situ hemostatic therapy, which includes implantable devices combined with dry materials that are activated by the presence of aqueous physiological fluids. The combination of an implantable device with dry materials may ensure in situ hemostatic therapy will occur at the site of implantation.

In embodiments, an implant in accordance with the present disclosure may be a surgical patch. The surgical patch may be configured so that it is capable of surrounding tubular structures of various sizes in situ. In embodiments, the surgical patch may include a longitudinal slit. Additional slits may extend from the longitudinal slit. These slits may form retractable flaps that may be retracted for placement in situ and folded back over the location of, for example, a bleeding area. In other embodiments, the surgical patch may include one or more through-holes or cut-outs for placement of the patch around various tissues in situ. In addition, the patch may be coated and/or impregnated with materials, such as, precursors, that will form a hydrogel in situ. These hydrogels may further promote hemostasis and/or assist in adhering the patch to tissue.

Although the following description is with reference to a hemostatic patch, the patch described herein may be any surgical patch and is not limited to patches capable of conferring hemostasis.

Figure 1:
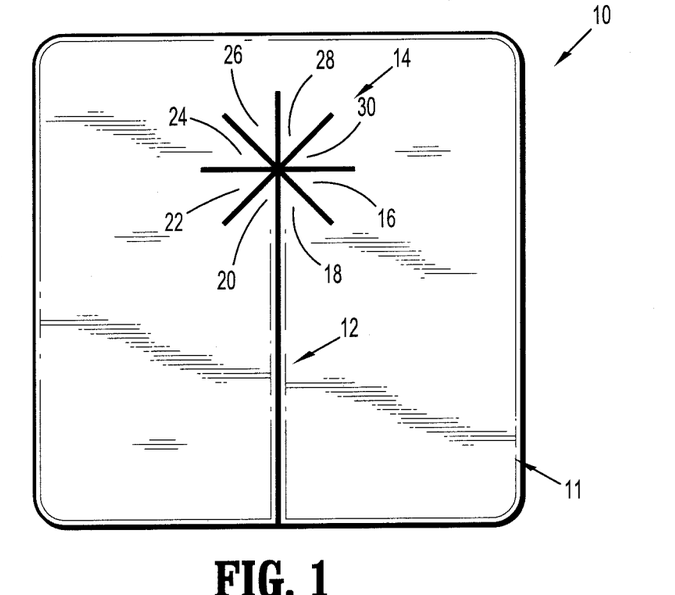
FIG. 1 is an illustration of an embodiment of a hemostatic patch of the present disclosure possessing flaps.

Referring now in detail to the drawings, in which like reference numerals are applied to like elements in the various views, FIG. 1 depicts a hemostatic patch 10 including a body 11, a longitudinal slit 12 bisecting a portion of body 11, and additional slits extending from the longitudinal slit 12, forming a star pattern 14, which defines retractable sections 16, 18, 20, 22, 24, 26, 28, and 30. As is apparent from FIG. 1, the additional slits extending from the longitudinal slit may define the number of retractable sections.

The longitudinal slit 12 and additional slits forming star pattern 14 are cuts through the body 11 of hemostatic patch 10. These slits may be formed without removing any portion of the body 11 of hemostatic patch 10, i.e., the body 11 may be contiguous. In embodiments, the slits may be perforated, rather than cut through, so that certain sections may be retracted while other sections are more securely maintained in their original position. The longitudinal slit 12 extends from an edge of the body 11 and may bisect from about 1% to about 99% of the length of the body 11, in embodiments from about 25% to about 75% of the length of the body 11. In embodiments, the additional slits may be from about 10% to about 75% of the length of the longitudinal slit, in embodiments from about 25% to about 50% of the length of the longitudinal slit.

Any number of additional slits may extend from the longitudinal slit. For example, in embodiments, the implant may include one additional slit. In other embodiments, the implant may include, for example, 20 or more additional slits. In some cases there may be from about 2 to about 10 additional slits. The additional slits may be at any angle extending from the longitudinal slit. For example, an additional slit may extend at an angle from about 1° to about 179° from the longitudinal slit. Where there is more than one additional slit, the additional slits may extend from the longitudinal slit at angles that are the same, i.e., each additional slit may be angled equally from those to either side of it, or different angles.

Figure 2:
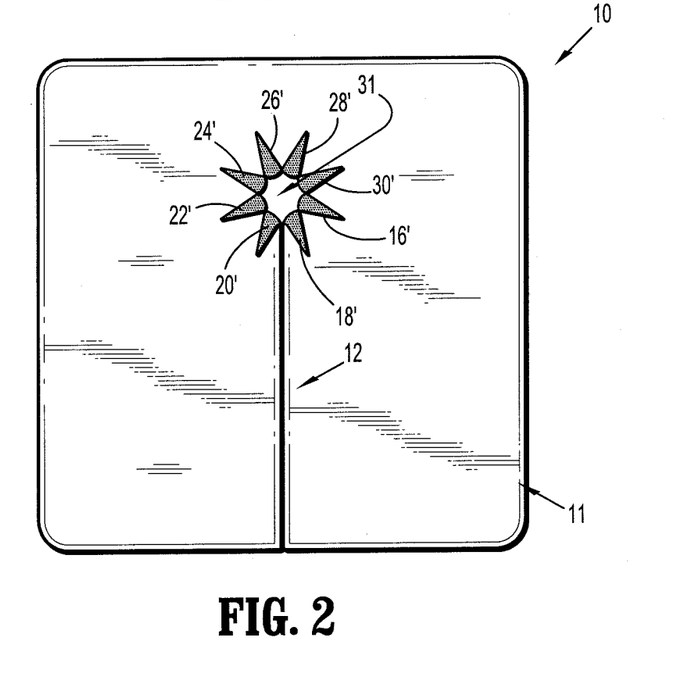
FIG. 2 is an illustration of the hemostatic patch of FIG. 1 with some of the flaps retracted.

As noted above, the slits form retractable sections or flaps. As shown in FIG. 2, sections 16, 18, 20, 22, 24, 26, 28, and 30 may be opened (or retracted) to form retractable flaps 16', 18', 20', 22', 24', 26', 28', and 30', and through-hole 31. In accordance with the present disclosure a "through-hole" goes completely through the hemostatic patch, thereby creating an opening. In embodiments, no portion of the body 11 is removed in order to create the through-hole 31; rather, the through-hole 31 is formed by retracting the retractable flaps 16', 18', 20', 22', 24', 26', 28', and 30'. Although depicted with eight retractable sections, any number of retractable sections may be included in the hemostatic patch 10.

Figure 3:
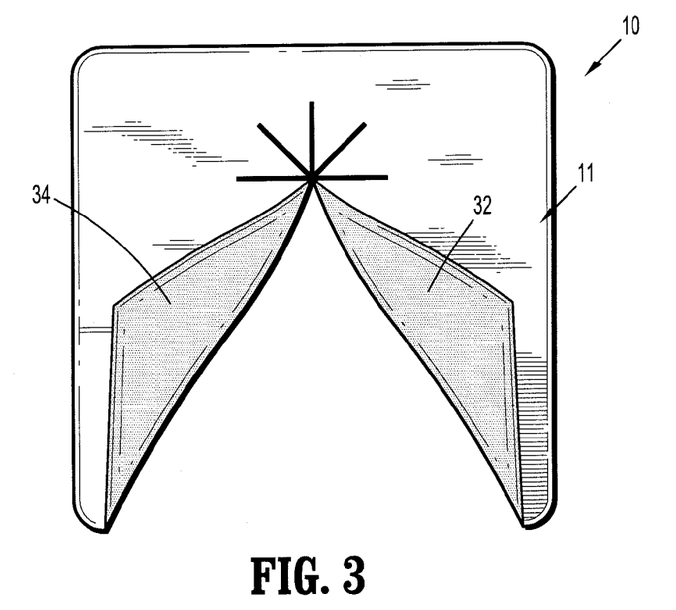
FIG. 3 is an illustration of the hemostatic patch of FIG. 1 with longitudinal flaps retracted.
Figure 4:
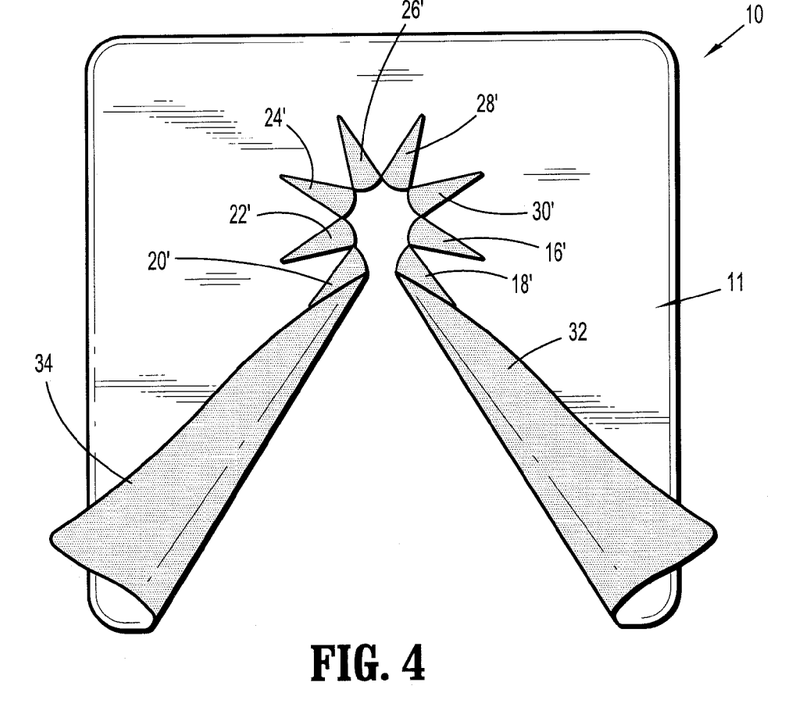
FIG. 4 is an illustration of the hemostatic patch of FIG. 1 with additional flaps and the longitudinal flaps retracted.

FIG. 3 depicts hemostatic patch 10 with longitudinal slit 12 retracted or folded back to form retractable flaps 32 and 34. The retractable flaps allow the hemostatic patch 10 to surround tissue prior to contacting the tissue. FIG. 4 depicts all of the flaps 32, 34, 16', 18', 20', 22', 24', 26', 28', and 30' retracted to create a large opening in the body 11 of the hemostatic patch 10.

When folded back, the flaps may prevent hydrogel precursors on the patch from coming into contact with moist tissue surface until the surgical patch is in place. Then the flaps may be folded back onto the tissue to surround and seal the tubular tissue to prevent further bleeding. The cut-outs and through-holes allow for hemostasis around uniquely shaped tissues in situ. This function may be useful, for example, during a surgical procedure such as an anastomosis procedure. During a surgical anastomosis, two tubular structures or hollow tissues are joined in situ. For example, a surgical anastomosis may include: joining two blood vessels during bypass surgery, including a procedure known as coronary artery bypass grafting; resectioning a portion of intestine following removal of an intestinal segment; reversal of tubal ligation or vasectomy procedures; restoration of continuity to the bladder; and the like.

A hemostatic patch with a star pattern may be useful, in embodiments, in an end-to-side vascular anastomosis. For example, hemostatic patches in sheet form may not be easily applied to an end-to-side vascular anastomosis due to the complex geometry involved at the site of the anastomosis. Moreover, if the material utilized to form the hemostatic patch is not compliant enough, it may be stretched around the anastomosis suture line, but a risk of compression and/or stenosis arises. Small strips may be cut and placed on the suture line, but this may be very time intensive, and overlapping strips may lead to gaps, which may allow bleeding to continue.

Figure 5A:
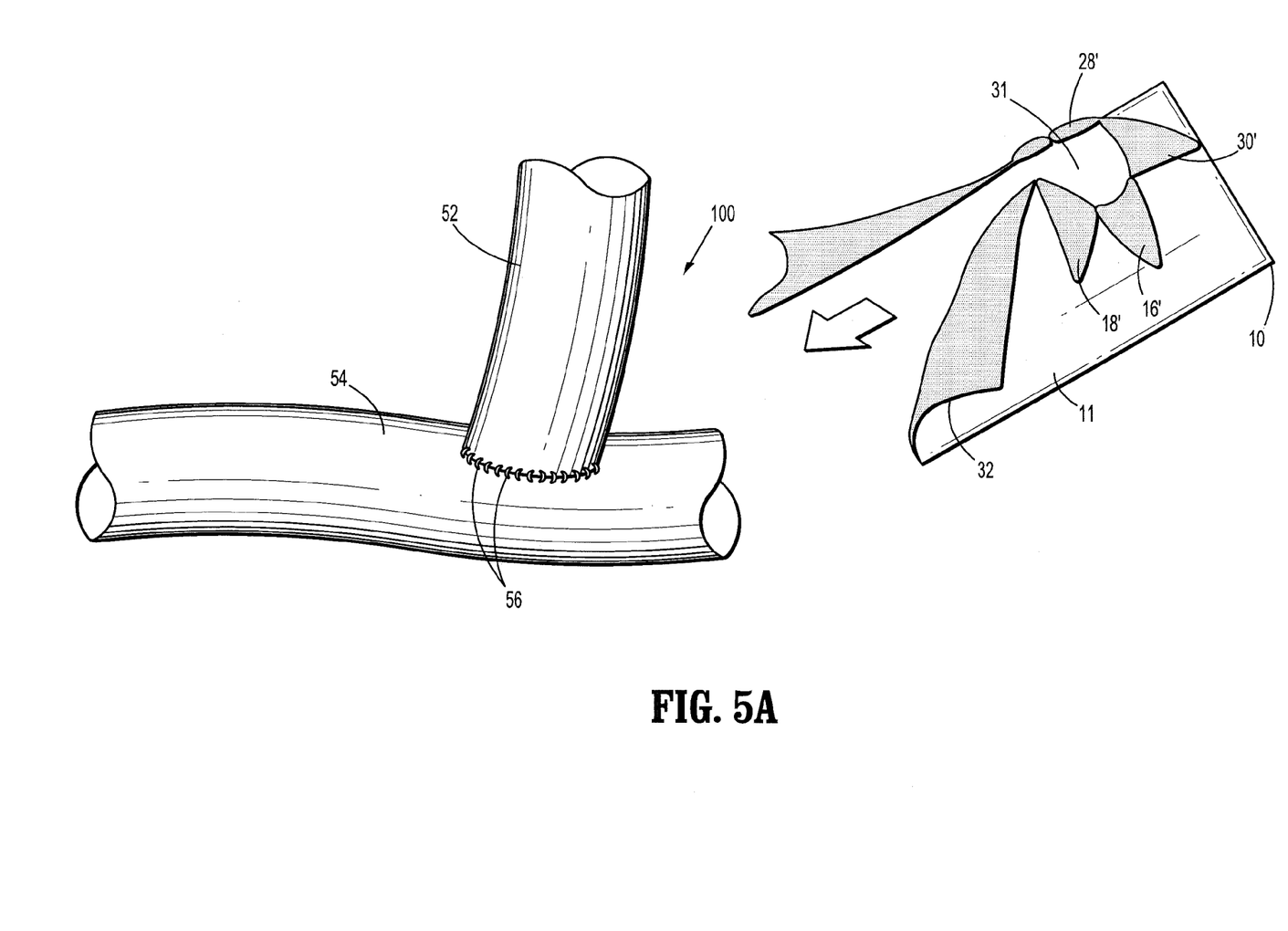
FIG. 5A is a side view of the hemostatic patch of FIG. 1, folded with flaps retracted for positioning over a surgical anastomosis.
Figure 5B:
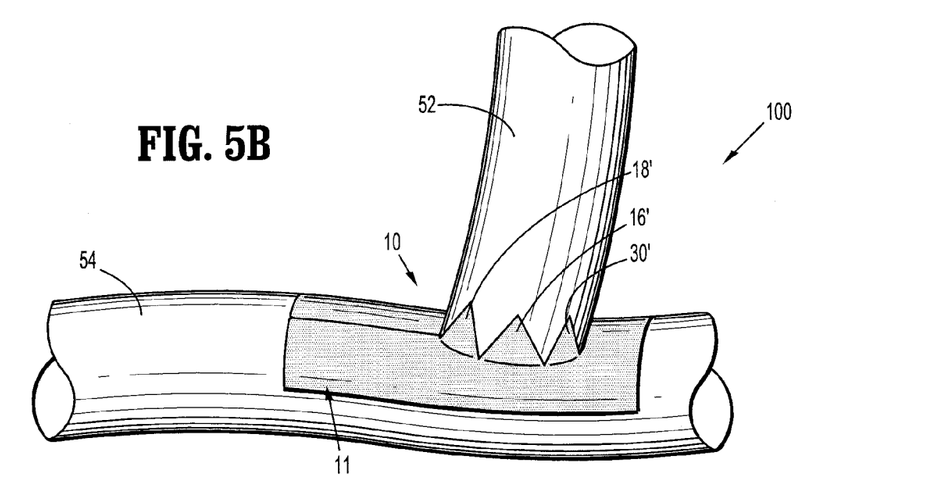
FIG. 5B is a side view of the surgical anastomosis having the hemostatic patch of FIG. 1 positioned thereover.

An example of a vascular anastomosis 100 is shown in FIG. 5A. A blood vessel 52 is joined to a blood vessel 54 using sutures or staples 56. The flaps 32, 18', 16', 30', 28' (shown) and 34, 20', 22', 24', 26' (not shown) of the body 11 of the hemostatic patch 10 are retracted in order to prevent contact with the vessels 52 and 54, prior to locating the hemostatic patch 10 around the intersection of the vessels 52 and 54. As shown in FIG. 5B, when placed around the anastomosis 100, the body 11 surrounds the intersection of vessels 52 and 54 (shown) and 28', 20', 22', 24' and 26' (not shown). The body 11 of the hemostatic patch 10 is coplanar with vessel 54. Flaps 16', 18' and 30' (shown) and 28', 20', 22', 24', and 26' (not shown) are retracted from the plane of the body 11 and abut vessel 52.

Figure 6:
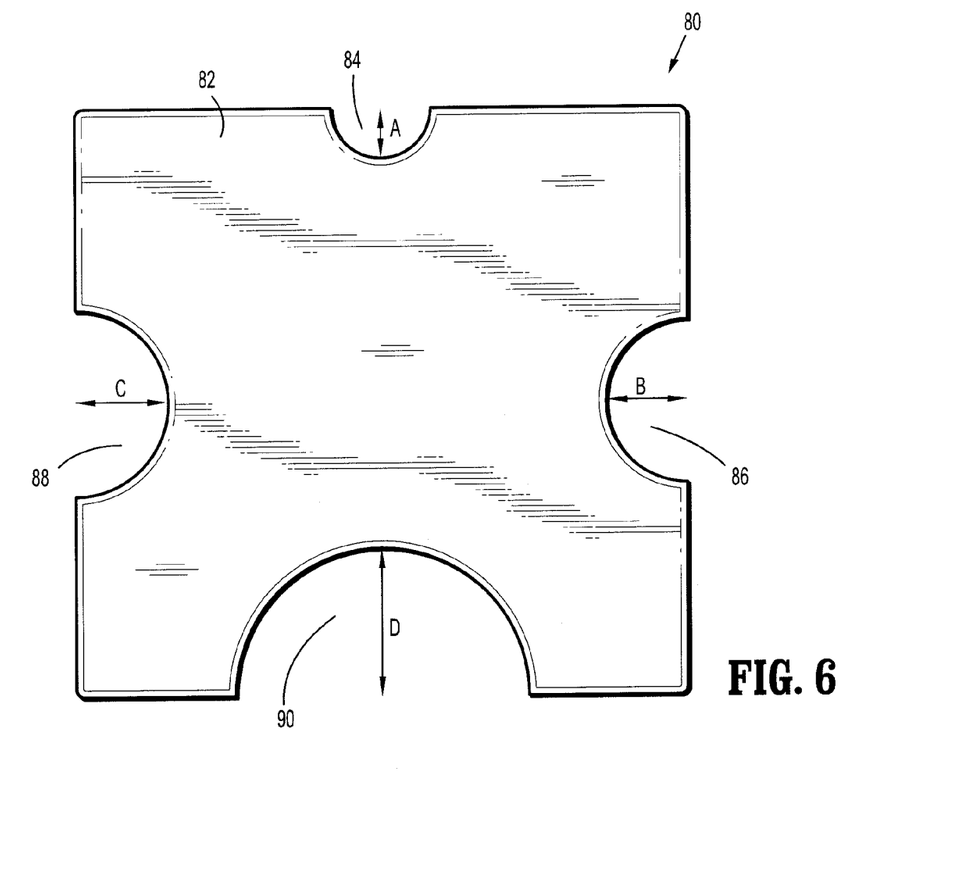
FIG. 6 is an illustration of yet another embodiment of a hemostatic patch in accordance with the present disclosure.

FIG. 6 depicts yet another embodiment of an implant of the present disclosure. A hemostatic patch 80 may include body 82 and arcuate cut-outs 84, 86, 88, and 90. The arcuate cut-outs 84, 86, 88, and 90 each have a depth A, B, C, and D, respectively. The depths A, B, C, D, are the distance between the edge of the body 82 of the hemostatic patch and the innermost portion of the arcuate cut-out 84, 86, 88, and 90, respectively, and may be the same or different for each arcuate cut-out 84, 86, 88, and 90. For example, where the depth is different, in embodiments depth A may be about 2 mm, depth B about 3 mm, depth C about 4 mm, and depth D about 5 mm. In other embodiments, the depth of, for example, cut-outs 84 and 90, or 88 and 86, may be the same.

Figure 7:
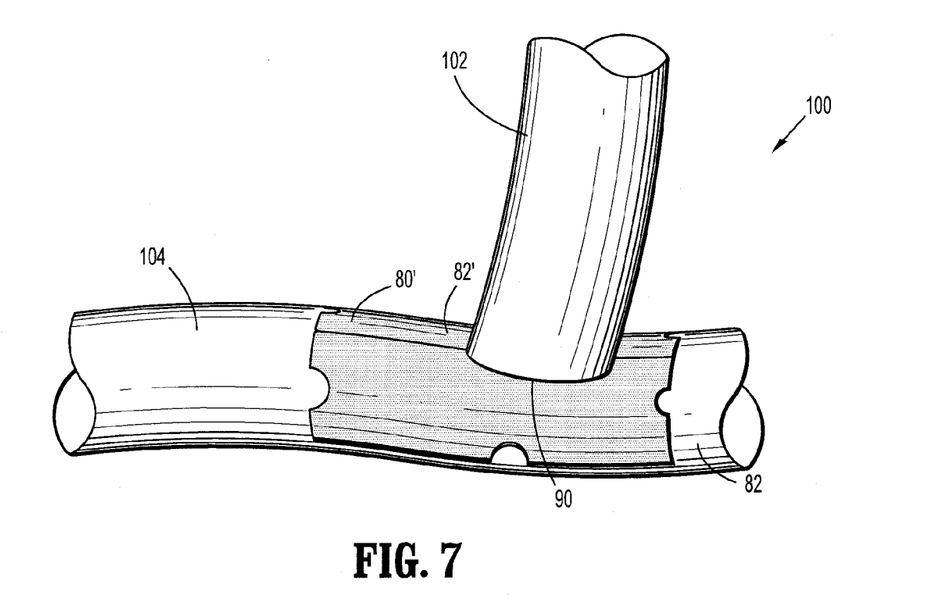
FIG. 7 is an illustration of a surgical anastomosis having two of the hemostatic patches of FIG. 6 applied thereto.
Figure 8:
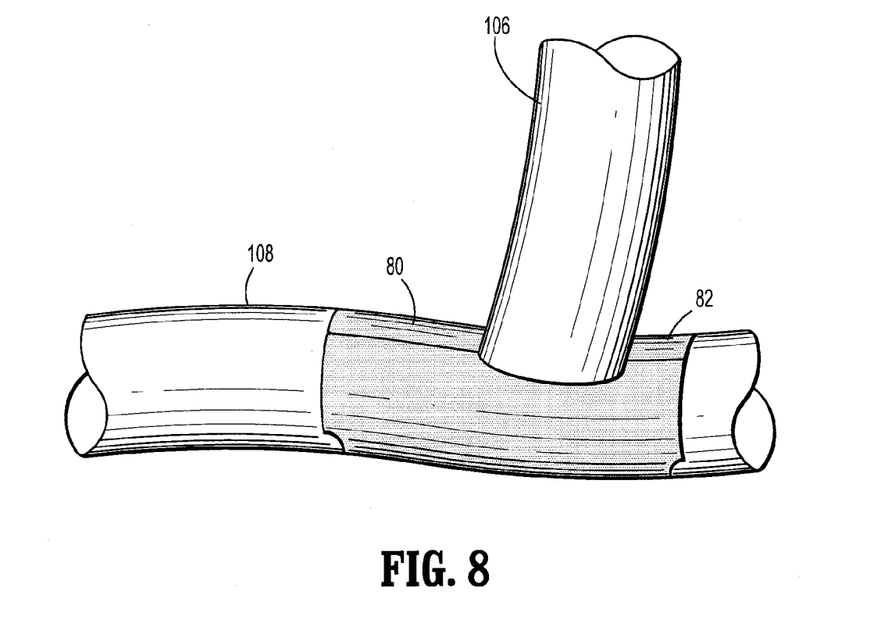
FIG. 8 is an illustration of a surgical anastomosis with one of the hemostatic patches of FIG. 6.

As shown in FIG. 7 a vascular anastomosis 100 may be formed from tissues 102 and 104. Two hemostatic patches from FIG. 6, 80 and 80', may be aligned so that arcuate cut-outs 90 and 90' (not shown) encircle tissue 102 and bodies 82 and 82' lie along, adhere to, and are coplanar with tissue 104. FIG. 8 depicts an embodiment where the depths A and D of arcuate cut-outs 84 and 90, respectively, are the same. The body 82 of hemostatic patch 80 may surround tissue 108 and arcuate cut-outs 84 and 90 may encircle tissue 106.

Figure 9:
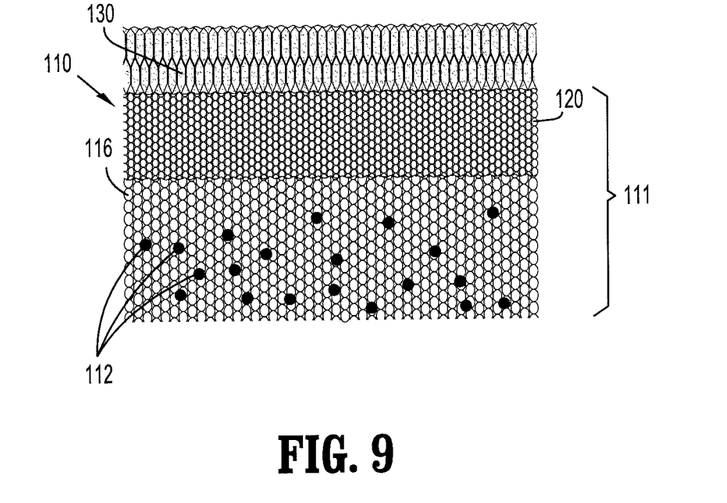
FIG. 9 is an enlarged illustration of a portion of a hemostatic patch in accordance with the present disclosure.

FIG. 9 depicts a body 111 of a hemostatic patch 110 of the disclosure. The body 111 is made of a porous or fabric-like material or substrate 116. The porous substrate 116 has a first hydrogel precursor 112 applied to a first portion and a second hydrogel precursor 120 applied to a second portion. Such a hemostatic patch 110 is disclosed in U.S. patent application Ser. No. 12/573,176, filed Oct. 5, 2009, the entire disclosure of which is incorporated by reference herein. The body 111 of FIG. 9 is shown having a first hydrogel precursor 112 in the form of particles applied to a first portion of the porous substrate or fabric-like material 116 and a second hydrogel precursor 120 in the form of a film applied to a second portion of the porous substrate 116.

During use, the hemostatic patch 110 is oriented with the second portion of the body 111, to which the second hydrogel precursor 120 is applied, being closer to the tissue 130, and the first portion having the first hydrogel precursor 112 applied thereto further from the tissue 130. In embodiments, the first and second portions may be distinguishable from one another by the addition of contrast dyes, surface texturing, coloring or other visual cues. Upon contact with tissue, such as, for example, injured tissue 130, the hemostatic patch 110 will soak up physiological fluid and the second hydrogel precursor 120 may be dissolved by the fluid. As the fluid wicks into and migrates across the body 111 of the hemostatic patch 110, it will carry the dissolved second hydrogel precursor 120 along through the hemostatic patch 110. Eventually, the fluid will migrate through the body 111 sufficiently to reach the first portion to which the first hydrogel precursor 112 is applied, thereby contacting the first hydrogel precursor 112. The first and second hydrogel precursors 112, 120 will then react to form a biocompatible cross-linked material, thereby creating hemostasis at the injury site. In some embodiments, the biocompatible cross-linked material produced by reaction of the first and second hydrogel precursors 112, 120 will not only provide hemostatic properties but also provide a portion of the hemostatic patch 110 with adhesive properties.

The porous substrate 116 of the body 111 of the hemostatic patch 110 has openings or pores over at least a portion of a surface thereof. The pores may be formed in the substrate either before or after implantation. As described in more detail below, suitable materials for forming the porous substrate include, but are not limited to fibrous structures (e.g., knitted structures, woven structures, non-woven structures, etc.) and/or foams (e.g., open or closed cell foams). In embodiments, the pores may be in sufficient number and size so as to interconnect and thus span across the entire thickness of the porous substrate. Woven fabrics, kitted fabrics and open cell foam are illustrative examples of structures in which the pores can be in sufficient number and size so as to interconnect across the entire thickness of the porous substrate. In embodiments, the pores do not interconnect across the entire thickness of the porous substrate. Closed cell foam or fused non-woven materials are illustrative examples of structures in which the pores may not interconnect across the entire thickness of the porous substrate. In other embodiments, the pores of the porous substrate may span across the entire thickness of porous substrate. In yet other embodiments, the pores do not extend across the entire thickness of the porous substrate, but rather are present at a portion of the thickness thereof. In embodiments, the openings or pores are located on a portion of the surface of the porous substrate, with other portions of the porous substrate having a non-porous texture.

In other embodiments, the pores may be formed after implantation in situ. The in situ pore formation may be performed using any suitable method. Some non-limiting examples include the use of contact lithography, living radical photopolymer (LRPP) systems, salt leaching, combinations thereof, and the like. Those skilled in the art reading the present disclosure will envision other pore distribution patterns and configurations for the porous substrate.

Where the porous substrate is fibrous, the fibers may include filaments or threads suitable for knitting or weaving or may be staple fibers, such as those frequently used for preparing non-woven materials. The fibers may be made from any biocompatible material. Thus, the fibers may be formed from a natural material or a synthetic material. The material from which the fibers are formed may be bioabsorbable or non-bioabsorbable. It should be understood that any combination of natural, synthetic, bioabsorbable and non-bioabsorbable materials may be used to form the fibers.

Some non-limiting examples of materials from which the fibers may be made include, but are not limited to, polyesters such as poly(lactic acid) and poly(glycolic acid) poly(trimethylene carbonate), poly(dioxanone), poly(hydroxybutyrate), poly(phosphazine), polyethylene terephthalate, ultra-high molecular weight polyethylene, polyethylene glycols, polyethylene oxides, polyacrylamides, polyhydroxyethylmethylacrylate (pHEMA), polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, poly(saccharides), polyamides, poly(iminocarbonates), polyalkylene oxalates, polyoxaesters, polyorthoesters, polyphosphazenes, biopolymers, polymer drugs and copolymers, block copolymers, homopolymers, blends and combinations thereof.

Where the porous substrate is fibrous, the porous substrate may be formed using any method suitable to forming fibrous structures including, but not limited to, knitting, weaving, non-woven techniques, wet-spinning, electro-spinning, extrusion, co-extrusion, and the like. Suitable techniques for making fibrous structures are within the purview of those skilled in the art. In embodiments, the textile has a three dimensional structure, such as the textiles described in U.S. Pat. Nos. 7,021,086 and 6,443,964, the entire disclosures of each of which are incorporated by reference herein.

In some embodiments, the porous substrate is made from fibers of oxidized cellulose. Such materials are known and include oxidized cellulose hemostat materials commercially available under the trade name SURGICEL®. Methods for preparing oxidized cellulose hemostat materials are within the purview of those skilled in the art and are disclosed, for example, in U.S. Pat. Nos. 3,364,200; 4,626,253; 5,484,913; and 6,500,777, the entire disclosures of each of which are incorporated by reference herein.

Where the porous substrate is a foam, the porous substrate may be formed using any method suitable to forming a foam or sponge including, but not limited to, the lyophilization or freeze-drying of a composition. The foam may be cross-linked or non-cross-linked, and may include covalent or ionic bonds. Suitable techniques for making foams are within the purview of those skilled in the art.

As mentioned above, the porous substrate 116 has a first and second hydrogel precursor 112, 120 applied thereto. The terms "first hydrogel precursor" and "second hydrogel precursor" each mean a polymer, functional polymer, macromolecule, small molecule, or crosslinker that can take part in a reaction to form a network of crosslinked molecules, e.g., a hydrogel.

In embodiments, each of the first and second hydrogel precursors 112, 120, include only one category of functional groups, for example only nucleophilic groups or only electrophilic functional groups, so long as both nucleophilic and electrophilic precursors are used in the crosslinking reaction. Thus, for example, if the first hydrogel precursor 112 has nucleophilic functional groups such as amines, the second hydrogel precursor 120 may have electrophilic functional groups such as N-hydroxysuccinimides. On the other hand, if first hydrogel precursor 112 has electrophilic functional groups such as sulfosuccinimides, then the second hydrogel precursor 120 may have nucleophilic functional groups such as amines or thiols. Thus, functional polymers such as proteins, poly(allyl amine), styrene sulfonic acid, or amine-terminated di- or multifunctional poly(ethylene glycol) ("PEG") can be used.

The first and second hydrogel precursors 112, 120 may have biologically inert and water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly (vinyl pyrrolidinone) ("PVP"); poly(amino acids); poly (saccharides), such as dextran, chitosan, alginates, carboxymethylcellulose, oxidized cellulose, hydroxyethylcellulose, hydroxymethylcellulose, hyaluronic acid, and proteins such as albumin, collagen, casein, and gelatin. The polyethers, and more particularly poly(oxyalkylenes), poly(ethylene glycol) or polyethylene glycol, are especially useful. When the core is small in molecular nature, any of a variety of hydrophilic functionalities can be used to make the first and second hydrogel precursors 112, 120 water soluble. For example, functional groups like hydroxyl, amine, sulfonate and/or carboxylate, which are water soluble, may be used to make the precursor water soluble. As a further example, the N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

The first and second hydrogel precursors 112, 120 may be applied to the porous substrate 116 using any suitable method within the purview of those skilled in the art. For example, the first and second hydrogel precursors 112, 120, may be incorporated into the porous substrate 116 prior to forming the porous substrate 116. In another non-limiting example, the first or second hydrogel precursors 112, 120 may be positioned in the pores of the porous substrate 116 or onto a surface of the porous substrate 116 following formation of the substrate. In additional embodiments, the porous substrate 116 may be calendered prior to application of the first hydrogel precursor 112 thereby allowing the first or second hydrogel precursors 112, 120 to penetrate into openings on the substrate which were created by the calendaring process.

In other embodiments, the first or second hydrogel precursors may be in the form of a coating which is applied to the substrate in any concentration, dimension and configuration capable of forming the hemostatic patch. The coating may form a non-porous layer or a porous layer. In embodiments, at least one of the first and second hydrogel precursors is a cross-linker. In embodiments, at least one of the first and second hydrogel precursors is a macromolecule, and may be referred to herein as a "functional polymer".

Each of the first and second hydrogel precursors is multifunctional, meaning that it includes two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form cross-linked polymeric products.

In embodiments, a multifunctional nucleophilic polymer such as trilysine may be used as a first hydrogel precursor and a multifunctional electrophilic polymer such as a multi-arm PEG functionalized with multiple NHS groups may be used as a second hydrogel precursor. The multi-arm PEG functionalized with multiple NHS groups can for example have four, six or eight arms and have a molecular weight of from about 5,000 to about 25,000. Other examples of suitable first and second hydrogel precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated by reference herein.

While the present disclosure may involve a hemostatic patch, any surgical patch may be used. The hemostatic patch may be any size and dimension. In embodiments the patch may be capable of transport in a laparoscopic deployment device or capable of introduction in open surgery. In embodiments, the hemostatic patch may be about 2 inches square, although it is envisioned that the patch may be of varying shapes and sizes. Additionally, while the substrate used in forming the patch is described as "porous," the substrate may be porous or non-porous in various embodiments.

Upon application to a site of bleeding tissue, the hemostatic patch may affect hemostasis of said tissue. As used herein, the term "hemostasis" means the arrest of bleeding. It is believed, without being limited to any theory, that the hemostatic effect of the hemostatic patch is due to both intrinsic and extrinsic factors. In embodiments, the substrate may include a hemostatic agent providing an intrinsic hemostatic effect. In other embodiments, the cross-linking between the hydrogel precursors creates a physical barrier to blood flow, thereby providing an extrinsic hemostatic effect.

Hemostasis may occur, at the site of application of the hemostatic patch, within less than about 2 minutes. As stated above, upon contact with tissue, such as, for example, injured or bleeding tissue, the hemostatic patch soaks up interstitial and physiological fluid (e.g., blood, lymph-fluid, etc.) and the first and second hydrogel precursors are mixed by the fluid. In order to prevent the hemostatic patch from taking up fluid prior to use at the location in need of hemostasis, the hemostatic patch is retained or sealed in packaging until the time it is needed for its application.

Figure 10:
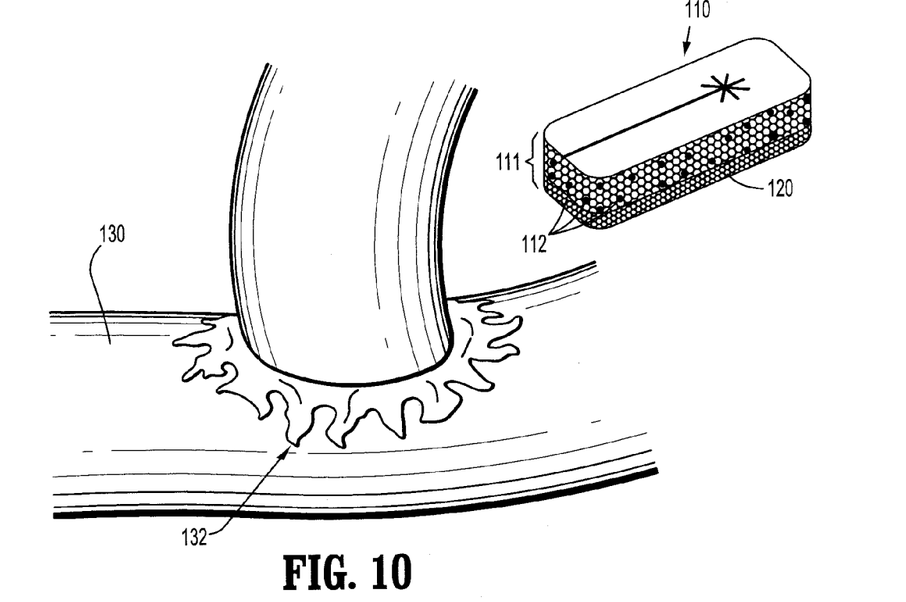
FIG. 10 is an enlarged illustration of a surgical anastomosis and a hemostatic patch in accordance with the present disclosure.
Figure 11:
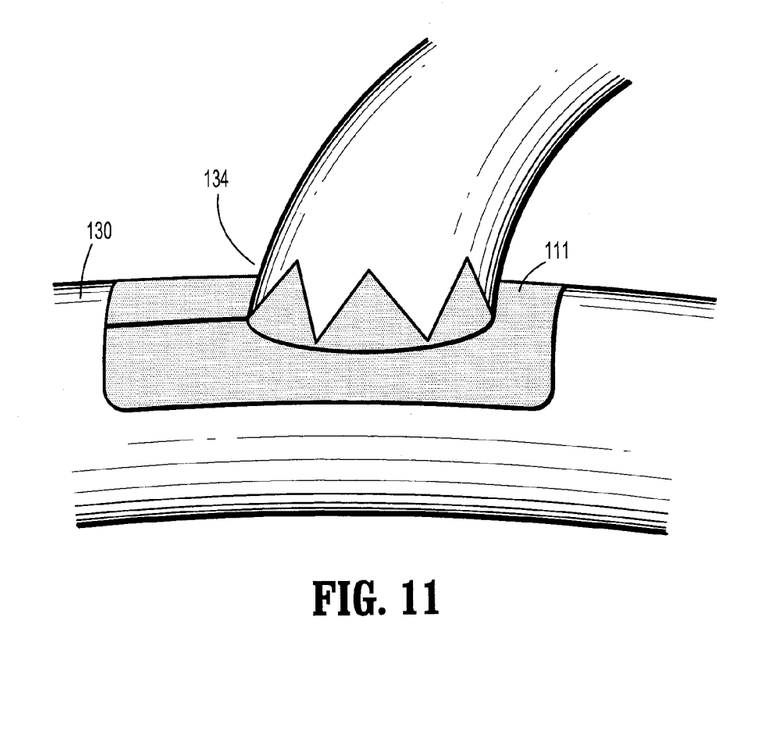
FIG. 11 is an enlarged illustration of a surgical anastomisis and a crosslinked hemostatic patch in accordance with the present disclosure.

As seen in FIG. 10, during use, the hemostatic patch 110 is oriented with second portion of body 111, to which the second hydrogel precursor 120 is applied, being closer to tissue 130 and with the first portion, to which the first hydrogel precursor 112 is applied, being disposed further from the tissue 130. Upon contact with bleeding tissue 130, hemostatic patch 110 soaks up physiological fluid or blood 132 and the second portion, having the second hydrogel precursor 120 is dissolved by the fluid or blood 132. As the fluid or blood 132 wicks into and migrates across the body 111 of the hemostatic patch 110, the fluid or blood carries the dissolved second hydrogel precursor 120 along through the body 111 sufficiently to reach the first portion, to which the first hydrogel precursor 112 is applied, thereby initiating the cross-linking reaction between the first and second hydrogel precursors 112, 120. At this point, as seen in FIG. 11, first and second hydrogel precursors 112, 120, then react to form a biocompatible cross-linked material 134 thereby assisting with the hemostasis of the tissue 130.

In use, an individual, such as a nurse or surgeon, using a hemostatic patch of the present disclosure may wish to cut the patch to a desired size and shape. For certain shapes, this may prove difficult and time consuming, and imperfect cuts may lead to continued bleeding where too much material has been cut away, so there is insufficient contact between the hemostat and tissue surface; vessel stenosis where too little material is removed; or a damaged patch that must be discarded.

Figure 12A:
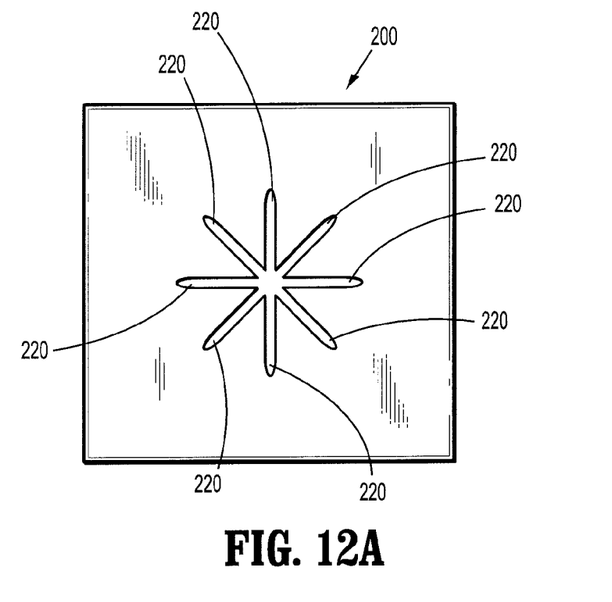
FIGS. 12A-C are illustrations of a template for cutting a hemostatic patch in accordance with the present disclosure.
Figure 12B:
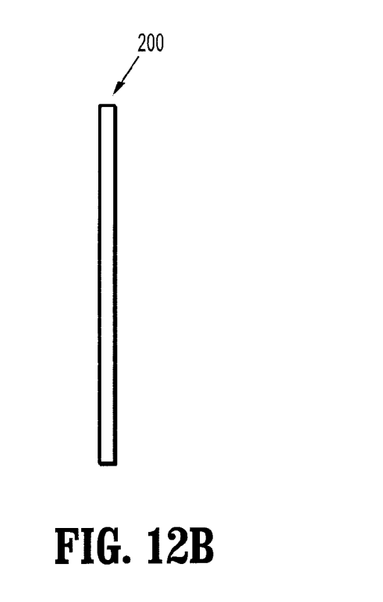
Figure 12C:
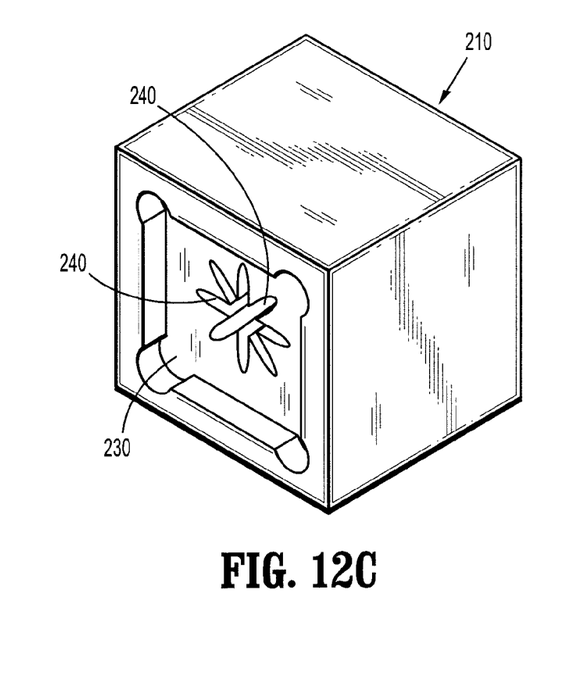

Thus, in embodiments, the hemostatic patch of the present disclosure may be provided with a cutting fixture, sometimes referred to herein, in embodiments, as a cutting template, which may allow one to cut the hemostatic patch to form a suitable pattern, in embodiments a star pattern, for application to a vascular anastomosis. For example, as set forth in FIGS. 12A-C, a template is provided having a top 200 and bottom 210 portions. In use, the template is opened by physically separating top 200 from bottom 210. A hemostatic patch (not shown) is placed in bottom 210 and top 200 is then affixed to bottom 210 by some means, including physical means such as a catch, snap, interference fit (like a twist), and/or hinge, or other means including magnets, combinations thereof, and the like. As seen in FIG. 12A, top 200 has narrow slits 220 cut in the shape of the star pattern, and top 200 can be thin, as depicted in the side view of top 200 set forth in FIG. 12B. Slits 220 are just wide enough to permit a scalpel blade, or some similar knife or cutting device, to pass through the openings, thereby permitting the scalpel blade to cut the hemostatic patch. As seen in FIG. 12C, the bottom 210 of the template has a recessed region 230 that holds the hemostatic patch in place and centers the hemostatic patch under the top 200 of the template. Additionally, bottom 210 of the template has a star pattern corresponding to the one in top 200, with openings 240 that are wider than the slits 220 included in the top 200 of the template. The openings 240 in bottom 210 of the template allow the scalpel blade to penetrate all the way through the hemostatic patch and template, while still providing sufficient support to the hemostatic patch. Once the pattern has been cut in the hemostatic patch, the top 200 is again removed from bottom 210, and the cut patch, now having a star pattern, is removed therefrom.

Figure 13A:
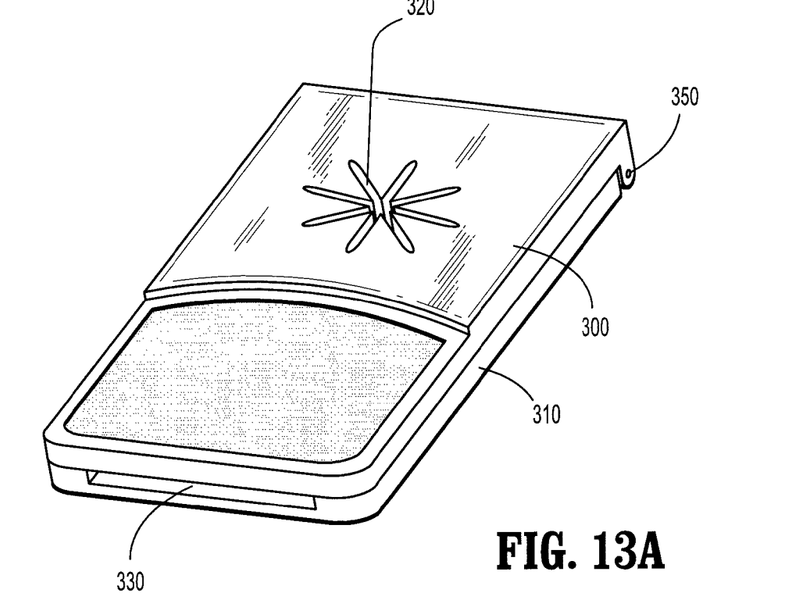
FIGS. 13A-B are illustrations of a template for cutting a hemostatic patch in accordance with the present disclosure.
Figure 13B:
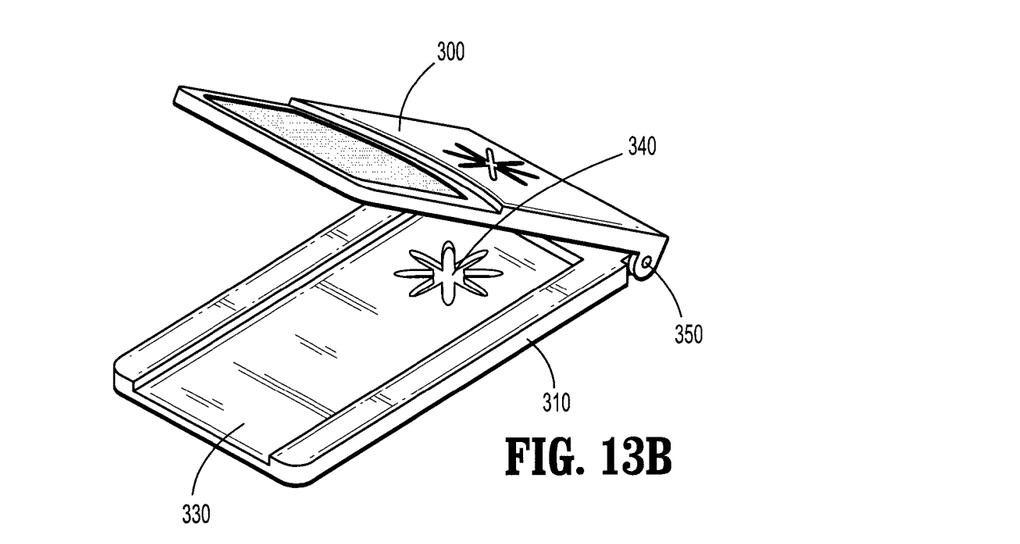

In other embodiments, as depicted in FIGS. 13A and 13B, top 300 may be connected to bottom 310 by hinge 350. Top 300 has slits 320 and bottom 310 has openings 340. A hemostatic patch (not shown) may be placed in a recessed portion 330 of bottom 310 to center the patch therein. After placement of the hemostatic patch in recessed portion 330 of bottom 310, top 300 is then closed, thereby holding the hemostatic patch firmly in place. An individual, such as a nurse or surgeon, may then pass a blade, including a scalpel or some similar knife or cutting device, through slits 320 in top 300, passing through opening 340 in bottom 310, thereby cutting a star pattern in the hemostatic patch. The top 300 is then opened, and the cut hemostatic patch, now having a star pattern, is removed from the template.

In embodiments, the template may have a handle or other similar region (not shown) to permit an individual to hold the template while keeping the individual's fingers away from the cutting zone.

The template of the present disclosure allows an individual, including a nurse or surgeon in an operating room, to cut a star pattern in a hemostatic patch of the present disclosure on an as-needed basis. The template is small, inexpensive, and easy to use.

While the above description has been directed to templates having a star pattern, thus permitting the formation of hemostatic patches having the same star pattern, templates for use in accordance with the present disclosure may possess any other desirable pattern (not shown) in tops 200 and/or 300, with corresponding patterns in bottoms 210 and/or 310, thereby permitting an individual to cut a hemostatic patch of the present disclosure in the desired pattern. Suitable patterns include, for example, an elongate longitudinal slit at least partially dividing a rectangular patch, or a modified keyhole like pattern, which includes the elongate slit as described above with a circular opening where the slit ends within the body of the patch.

Figure 14A:
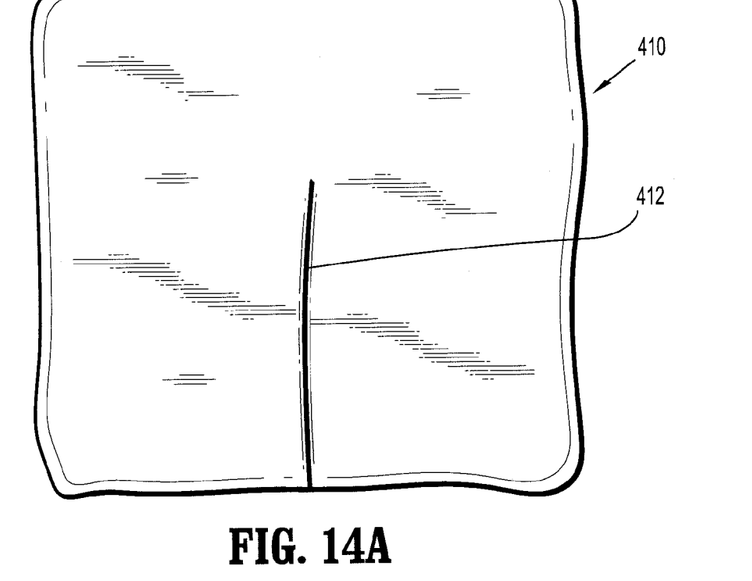
FIGS. 14A-B are illustrations of an embodiment of a hemostatic patch of the present disclosure possessing a longitudinal slit capable of forming flaps.
Figure 14B:
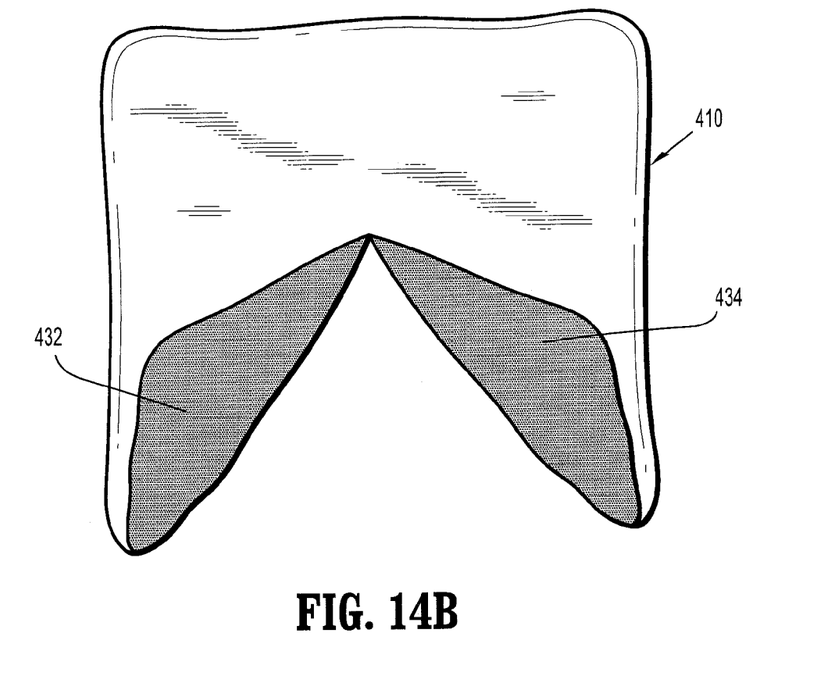

FIGS. 14A and 14B depict a hemostatic patch 410 of the present disclosure having elongate longitudinal slit 412 at least partly dividing patch 410. The longitudinal slit may be the same as longitudinal slit 12 described above with respect to hemostatic patch 10. As seen in FIG. 14A, in embodiments, longitudinal slit 412 may extend from an edge of hemostatic patch 410 to a point within the body of hemostatic patch 410. FIG. 14B depicts hemostatic patch 410 with longitudinal slit 412 retracted or folded back to form retractable flaps 432 and 434.

Figure 15A:
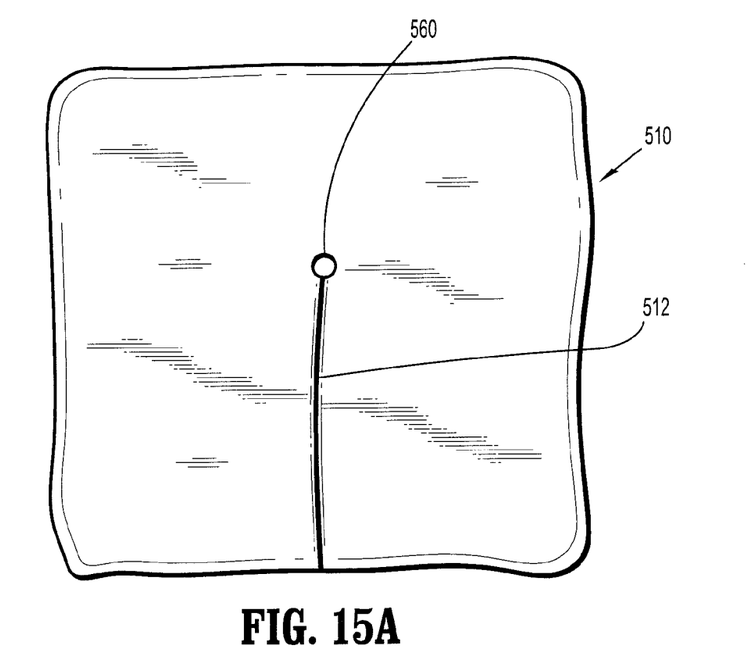
FIGS. 15A-B are illustrations of an embodiment of a hemostatic patch of the present disclosure possessing a keyhole configuration, including a longitudinal slit capable of forming flaps.
Figure 15B:
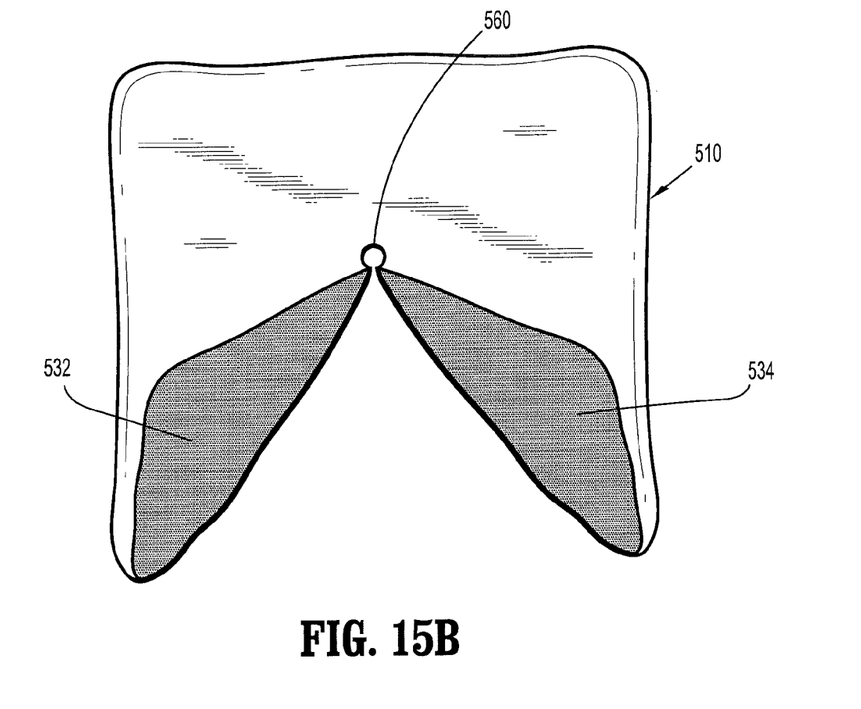

FIGS. 15A and 15B depict a hemostatic patch 510 of the present disclosure having elongate longitudinal slit 512 at least partly dividing patch 510. The longitudinal slit may be the same as longitudinal slit 12 described above with respect to hemostatic patch 10. As can be seen in FIG. 15A, longitudinal slit 512 extends from an edge of patch 510 into the body of patch 510, terminating at circular opening 560. Thus, hemostatic patch 510 may be referred to, in embodiments, as possessing a keyhole configuration. FIG. 15B depicts hemostatic patch 510 with longitudinal slit 512 retracted or folded back to form retractable flaps 532 and 534.

Additionally, the hemostatic patch may include biologically acceptable additives such as plasticizers, antioxidants, dyes, dilutants, therapeutic agents, and the like and combinations thereof, which can be coated on the filaments or fibers, or impregnated into the fibers or filaments (e.g., during compounding or extrusion) used to form the hemostatic patch of the present disclosure.

Therapeutic agents include, but are not limited to, drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons ($\beta$-IFN, $\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; cells, viruses, and ribozymes.

In embodiments, the therapeutic agent may include at least one of the following drugs, including combinations and alternative forms of the drugs such as alternative salt forms, free acid form, free base forms, pro-drugs and hydrates: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthmatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconizole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., ergotamine, propanolol, isometheptene mucate, and dichloralphenazone); sedatives/hypnotics (e.g., barbiturates such as pentobarbital, pentobarbital, and secobarbital; and benzodiazepines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encamide, digoxin, digitoxin, mexiletine, disopyramide phosphate, procainamide, quinidine sulfate, quinidine gluconate, quinidine polygalacturonate, flecamide acetate, tocamide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenyloin, phenyloin sodium, clonazepam, primidone, phenobarbitol, carbamazepine, amobarbital sodium, methsuximide, metharbital, mephobarbital, mephenyloin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, and methdilazine); agents useful for calcium regulation (e.g., calcitonin, and parathyroid hormone); antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, and epinephrine); anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate; steroidal compounds and hormones (e.g., androgens such as danazol, testosterone cypionate, fluoxymesterone, ethyltestosterone, testosterone enanthate, methyltestosterone); estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, glipizide, tolbutarnide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepam, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. In some embodiments, the therapeutic agent may be water soluble. In some embodiments, the therapeutic agent may not be water soluble.

In embodiments, the above therapeutic agents may be applied to a hemostatic patch of the present disclosure in a solution. Where the therapeutic agent is water soluble, water may be used as a solvent for forming such a solution. Other solvents which may be used include polar and non-polar solvents including, but not limited to, alcohols, such as, methanol, ethanol, propanol; chlorinated hydrocarbons such as methylene chloride, chloroform, 1,2-dichloro-ethane; and aliphatic hydrocarbons such as hexane, heptene, ethyl acetate; and the like and combinations of these.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A cutting template comprising:
   a top portion possessing at least one slit forming a desired pattern; and
   a bottom portion possessing openings corresponding to the pattern in the top portion, the bottom portion further comprising a recessed region capable of holding a surgical patch therein.

2. The cutting template of claim 1, wherein the recessed region is capable of holding the top portion.

3. The cutting template of claim 1, wherein the recessed region extends to an edge of the bottom portion and forms a slot capable of receiving the surgical patch between the top and bottom portion when the top portion is closed upon the bottom portion.

4. The cutting template of claim 1, wherein the openings in the bottom portion are wider than the at least one slit in the top portion.

5. The cutting template of claim 1, wherein the at least one slit in the top portion and the openings in the bottom portion are in a pattern capable of forming a hemostatic patch having a shape comprising a star.

6. The cutting template of claim 1, wherein the at least one slit in the top portion and the openings in the bottom portion are in a pattern capable of forming a hemostatic patch having a shape comprising a rectangular patch possessing an elongated longitudinal slit extending from an edge of the patch and at least partially dividing the patch.

7. The cutting template of claim 1, wherein the at least one slit in the top portion and the openings in the bottom portion are in a pattern capable of forming a hemostatic patch having a shape comprising a rectangular patch possessing an elongated longitudinal slit extending from an edge of the patch and terminating at a circular opening within the patch.

8. The cutting template of claim 1, further comprising a handle.

9. A cutting template comprising:
   a top portion possessing at least one slit forming a desired pattern; and
   a bottom portion possessing at least one slit, the bottom portion further comprising a recessed region capable of holding a surgical patch therein.

10. The cutting template of claim 9, wherein the recessed region is capable of holding the top portion.

11. The cutting template of claim 9, wherein the recessed region extends to an edge of the bottom portion and forms a slot capable of receiving the surgical patch between the top and bottom portion when the top portion is closed upon the bottom portion.

12. The cutting template of claim 9, wherein the at least one slit in the bottom portion is wider than the at least one slit in the top portion.

13. The cutting template of claim 9, further comprising a handle.

* * * * *